United States Patent
Nakamura et al.

[11] Patent Number: 6,113,853
[45] Date of Patent: Sep. 5, 2000

[54] STERILIZING AND RINSING WATER GENERATING METHOD AND APPARATUS THEREFOR

[75] Inventors: Shinichi Nakamura, Osaka; Kunihiko Fukuzuka, Habikino; Hiromi Fujii, Osaka, all of Japan

[73] Assignee: Omega Co., Ltd., Japan

[21] Appl. No.: 09/133,527

[22] Filed: Aug. 13, 1998

[30] Foreign Application Priority Data

Jul. 15, 1998 [JP] Japan .................................. 10-192476

[51] Int. Cl.$^7$ .................................................. A61L 2/18
[52] U.S. Cl. .............................. 422/23; 422/29; 422/37; 210/748; 210/754
[58] Field of Search ................................ 422/22, 23, 28, 422/29, 37; 205/556; 210/748, 754

[56] References Cited

U.S. PATENT DOCUMENTS 2,882,210  4/1959  Jenka ........................................ 204/151
5,429,723  7/1995  Atkinson .................................. 204/103
5,868,911  2/1999  Blum et al. .............................. 204/228

FOREIGN PATENT DOCUMENTS 0243846  4/1987  European Pat. Off. .......... C02F 1/46
3502068  5/1991  Japan ................................ C02F 1/46

*Primary Examiner*—Elizabeth McKane
*Attorney, Agent, or Firm*—Hayes, Soloway, Hennessey, Grossman & Hage PC

[57] ABSTRACT

In a sterilizing and rinsing water generating method of generating sterilizing and rinsing water by increasing the electric conductivity of water by adding halide electrolytes to the water and creating hypohalogenous acid by electrolyzing the water using an anode plate and a cathode, the mole ratio of bromide ions and chloride ions supplied by the electrolytes is set to 57:43 or a value in the vicinity of it. The sterilizing and rinsing water generated by the method can sterilize even germs which form spores having a high tolerance. There is also provided a sterilizing and rinsing water generating apparatus for embodying the method.

5 Claims, 13 Drawing Sheets

Table 1

| | | Mole ratio | | Processing temperature 20°C | | | Processing temperature 40°C | | |
|---|---|---|---|---|---|---|---|---|---|
| | | Br⁻ | Cl⁻ | 300ppm | 500ppm | | 300ppm | 500ppm | |
| Bacillius subtilis (ispores) | Processing time 15min. | 100 | 0 | 96 | 5.8 | | 21 | 0.9* | |
| | | 77 | 23 | 16 | 0.3* | | 3.2 | 0.1* | |
| | | 57 | 43 | 8 | 0.1* | | 1.5 | 0.0 | |
| | | 30 | 70 | 15 | 0.3* | | 2.7 | 0.1* | |
| | | 10 | 90 | 100 | 2.6 | | 12 | 0.5* | |
| | | 0 | 100 | 1020 | 21 | | 150 | 3.1 | |
| | | Br⁻ | Cl⁻ | 10ppm | 20ppm | 30ppm | 10ppm | 20ppm | 30ppm |
| Ordinary viable germs | Processing time 10sec. | 100 | 0 | 21 | 2 | 0.3* | 0.6* | 0 | 0 |
| | | 77 | 23 | 5 | 0.6* | 0.15* | 0.2* | 0 | 0 |
| | | 57 | 43 | 4 | 0.5* | 0.1* | 0.2* | 0 | 0 |
| | | 35 | 65 | 5 | 0.6* | 0.15* | 0.3* | 0 | 0 |
| | | 10 | 90 | 14 | 2 | 0.3* | 0.7* | 0 | 0 |
| | | 0 | 100 | 92 | 7 | 0.5* | 1.5 | 0 | 0 |
| | | Br⁻ | Cl⁻ | 10ppm | 10ppm** | 20ppm | 10ppm | 10ppm** | 20ppm |
| Group of colon bacilli | Processing time 10sec. | 100 | 0 | 3 | 0.70* | 0.05* | 0.30* | 0.00 | 0.00 |
| | | 77 | 23 | 0.4* | 0.15* | 0.00 | 0.10* | 0.00 | 0.00 |
| | | 57 | 43 | 0.3* | 0.10* | 0.00 | 0.00 | 0.00 | 0.00 |
| | | 43 | 57 | 0.4* | 0.15* | 0.00 | 0.05* | 0.00 | 0.00 |
| | | 30 | 70 | 0.5* | 0.20* | 0.00 | 0.10* | 0.00 | 0.00 |
| | | 10 | 90 | 1.5 | 0.50* | 0.05* | 0.20* | 0.00 | 0.00 |
| | | 0 | 100 | 6 | 2.0* | 0.05* | 0.30* | 0.00 | 0.00 |

* An average value is shown as it is, although it is intrinsically shown as zero.
** A processing time is set to 15 seconds.

STERILIZING AND RINSING WATER GENERATING METHOD AND APPARATUS THEREFOR

BACKGROUND OF THE INVENTION

1. Field of the Invention

The present invention relates to a sterilizing and rinsing water generating method and an apparatus therefor for sterilizing and rinsing human bodies such as hands and the like, foods and various kinds of equipment, clothing, environmental facilities and the like to which germs are liable to be deposited in hospitals, kitchens and the like.

2. Description of the Related Art

Conventionally, there is used an alkali aqueous solution in which sodium hypochlorous acid is dissolved in a prescribed concentration is used as sterilizing and rinsing water for sterilizing and rinsing human bodies such as hands and the like, foods and various kinds of equipment, clothing and environmental facilities such as passages to which germs are liable to be deposited in hospitals, kitchens and the like.

Since the alkali aqueous solution of sodium hypochlorous acid does not have a sufficient sterilizing capability in alkalinity, however, it must be acidified at any time. Thus, the alkali aqueous solution of sodium hypochlorous acid is not only troublesome in handling but also it does not have a sufficient sterilizing capability even if it is acidified.

To cope with the above problem, there is recently used a method of generating sterilizing and rinsing water by adding sodium chloride and inorganic acid to water and creating hypochlorous acid by electrolyzing the resulting water solution.

Although the sterilizing and rinsing water in which the hypochlorous acid is created has a sterilizing capability higher than that of the conventional sterilizing and rinsing water using sodium hypochlorous acid, a problem arises in that the sterilizing and rinsing water does not have a sufficient sterilizing capability to resistant germs such as MRSA, Helicobacter pylori, hepatitis B viruses, etc., which have turned into problems recently, and requires a long sterilizing time.

To cope with the above problem, Japanese Unexamined Patent Publication No. 3-502068 proposes a method of creating hypobromous acid which has a sterilizing capability higher than that of hypochlorous acid as a method of obtaining a higher sterilizing capability.

The hypobromous acid creating method proposed by Japanese Unexamined Patent Publication No. 3-502068 can provide the sterilizing capability higher than that obtained by the above method of creating hypochlorous acid by means of sodium chloride. However, since germs typically represented by *Bacillus subtilis, Clostridium botulinum*, Cryptosporidium, etc. that form spores have a very high tolerance, there is desired the development of sterilizing and rinsing water which has a higher sterilizing capability and is effective even to the germs which forms the spores, in view of the recent situation that food poisoning and hospital contamination caused by pathogenic *E coli* have turned into problems.

An object of the present invention made in view of the above problems is to provide a method of and an apparatus for generating sterilizing and rinsing water having a high sterilizing capability capable of sterilizing even germs which form spores having a high tolerance.

SUMMARY OF THE INVENTION

To solve the above problems, according to the present invention, there is provided a sterilizing and rinsing water generating method of generating sterilizing and rinsing water by increasing the electric coductivity of water by adding halide electrolytes to the water and creating hypohalogenous acid by electrolyzing the water using an anode plate and a cathode.

According to the present invention, it has been demonstrated that when the mole ratio of bromide ions and chloride ions in the water is set to 57:43 or a value in the vicinity of it, the sterilizing capability of the resultant sterilizing and rinsing water can be made higher than that of the sterilizing and rinsing water using simple bromide ions and further there can be obtained the highest effect among the systems containing the mixture of bromide ions and chloride ions.

Accordingly, it has been made possible to effectively sterilize not only various types of germs but also germs forming spores in a short time by using the mixing ratio.

In the sterilizing and rinsing water generating method of the present invention, it is preferable to set the hydrogen ion concentration i.e. the pH in the sterilizing and rinsing water to a range of 6–8.

With the above arrangement, the sterilizing and rinsing water which is obtained by setting the mole ratio of bromide ions and chloride ions in the water to 57:43 or a value in the vicinity of it has the highest sterilizing capability in the region of pH 6–8.

More specifically, the above mole ratio is the most effective ratio in the overall region of pH 6–8 which is a neutral region in which hands are less likely to become rough as well as a rinsing vessel, discharge pipe and various types of equipment which are in contact with the sterilizing and rinsing water are less likely to be corroded.

In the sterilizing and rinsing water generating method of the present invention, it is preferable that when the sterilizing and rinsing water is supplied to the outside, the electrolyzed water is heated to a prescribed temperature.

With this arrangement, when the temperature of the sterilizing and rinsing water to be supplied to the outside is increased and caused to come into contact with an object to be sterilized, it is possible to maintain the sterilizing power of the sterilizing and rinsing water for a prescribed period of time and then to increase the sterilizing capability thereof instantaneously and cause it to act on the object to be sterilized.

In the sterilizing and rinsing water generating method of the present invention, it is preferable that the electrolyzed water is diluted so that it is arranged as sterilizing and rinsing water having a prescribed hypohalogenous acid concentration and then supplied to the outside.

With this arrangement, since a larger amount of the sterilizing and rinsing water can be generated by electrolyzing a smaller amount of water, an apparatus can be reduced in size, sterilizing and rinsing water having a stable hypohalogenous acid concentration can be supplied and sterilization can be executed sufficiently.

A sterilizing and rinsing water generating apparatus of the present invention is characterized by comprising water supply means for supplying water; electrolyte mixing means disposed at a prescribed position in the water supply means for mixing bromide salt and chloride salt to the water or discharged water at a prescribed ratio so that the mole ratio of the bromide ions and the chloride ions in the water is set to 57:43 or a value in the vicinity of it; electrolyzing means disposed downstream of the electrolyte mixing means and having an anode plate and a cathode plate;

diluting means for diluting the electrolyzed water; free residual halogen concentration sensing means for sensing the free residual halogen concentration in the diluted water; and control means for controlling the dilution of the water based on the free residual halogen concentration sensed by the free residual halogen concentration sensing means so that the free residual halogen concentration in the water is set to a prescribed value.

According to the above characteristic, bromide salt and chloride salt are mixed with water at a prescribed ratio, bromide ions and chloride ions coexist in the water at the mole ratio of 57:43 or a value in the vicinity of it.

Accordingly, when hypochlorous acid and hypobromous acid are created by electrolyzing the water and the free residual halogen concentration of the water is set to a prescribed value, the sterilizing capability of the resultant sterilizing and rinsing water can be made higher than that of the sterilizing and rinsing water using simple bromide ions and achieve the highest sterilizing capability among the systems containing the mixture of bromide ions and chloride ions. In addition, the sterilizing and rinsing water can effectively sterilize germs which form spores in a short time.

It is preferable that the sterilizing and rinsing water generating apparatus of the present invention comprises pH sensing means for sensing the hydrogen ion concentration in the water and adding means for adding inorganic acid or an alkali aqueous solution to the water and the control means maintains the hydrogen ion concentration in the water to 6–8 by adding the inorganic acid or the alkali aqueous solution to the water by means of the adding means based on the hydrogen ion concentration sensed by the pH sensing means.

With this arrangement, the thus generated sterilizing and rinsing water has a hydrogen ion concentration (pH) maintained to pH 6–8 at all times that have the highest sterilizing capability and a higher sterilizing force than that of the sterilizing and rinsing water using simple bromine ions. Accordingly, the best sterilizing force can be drawn out of the resultant sterilizing and rinsing water and an effective sterilization can be carried out.

It is preferable that the sterilizing and rinsing water generating apparatus of the present invention comprises heating means for heating the water used to dilution to a prescribed temperature.

With this arrangement, the sterilizing capability of the sterilizing and rinsing water can be more enhanced by causing the sterilizing and rinsing water supplied from the sterilizing and rinsing water apparatus to come into contact with an object to be sterilized after the temperature thereof is increased.

TABLE 1 shows the results of a test of the sterilizing powers of the generated sterilizing and rinsing water.

DESCRIPTION OF THE PREFERRED EMBODIMENT

An embodiment of the present invention will be described below with reference to the drawings.

Figure 1:
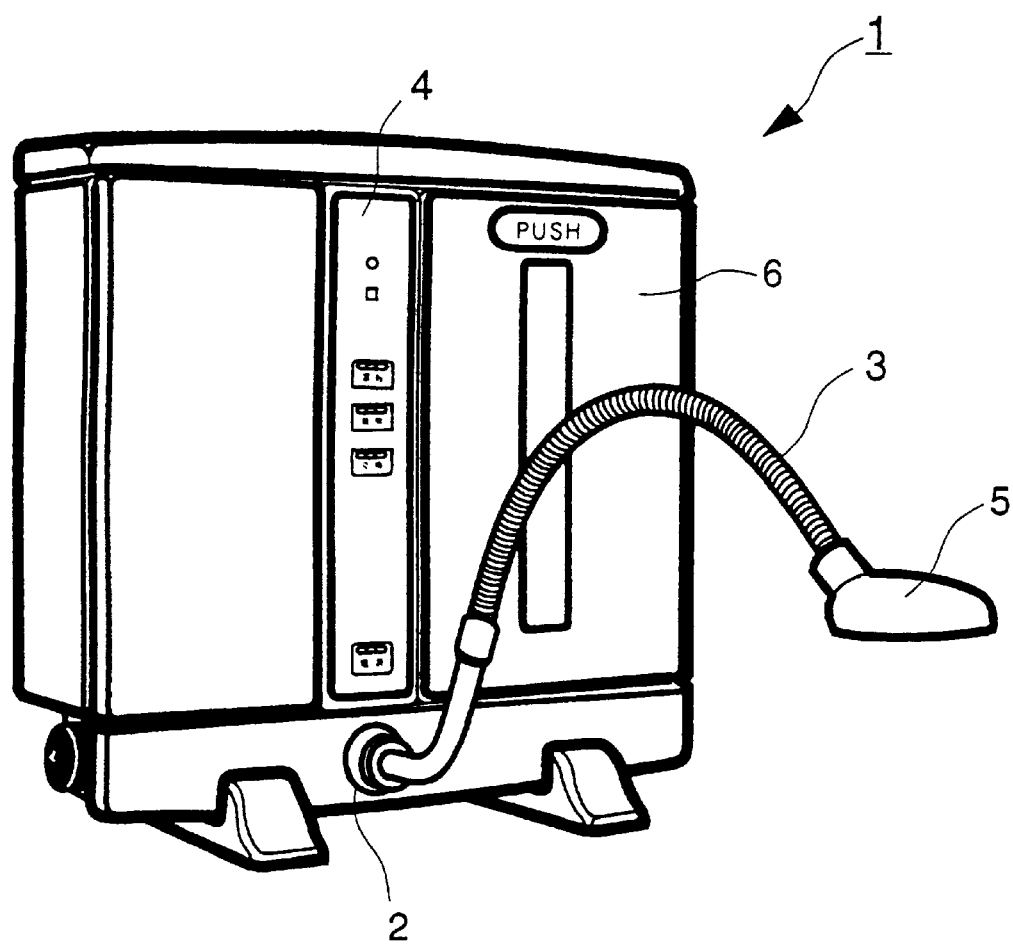
FIG. 1 is a perspective view showing the outside appearance of a sterilizing and rinsing water generating apparatus of an embodiment according to the present invention.
Figure 2:
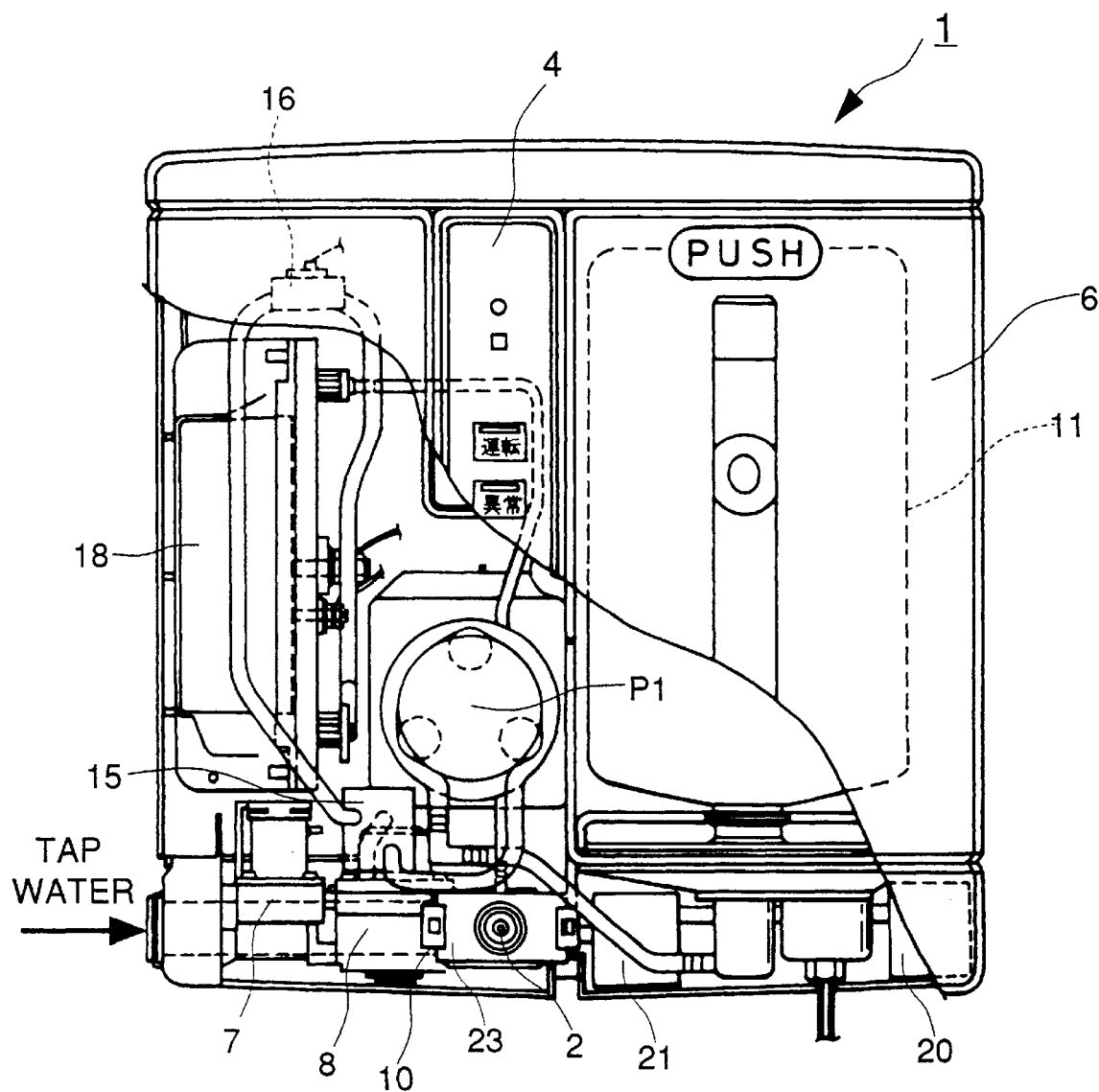
FIG. 2 is a side elevational view, partly in cross section, showing the inside arrangement of the sterilizing and rinsing water generating apparatus of the embodiment according to the present invention.
Figure 3:
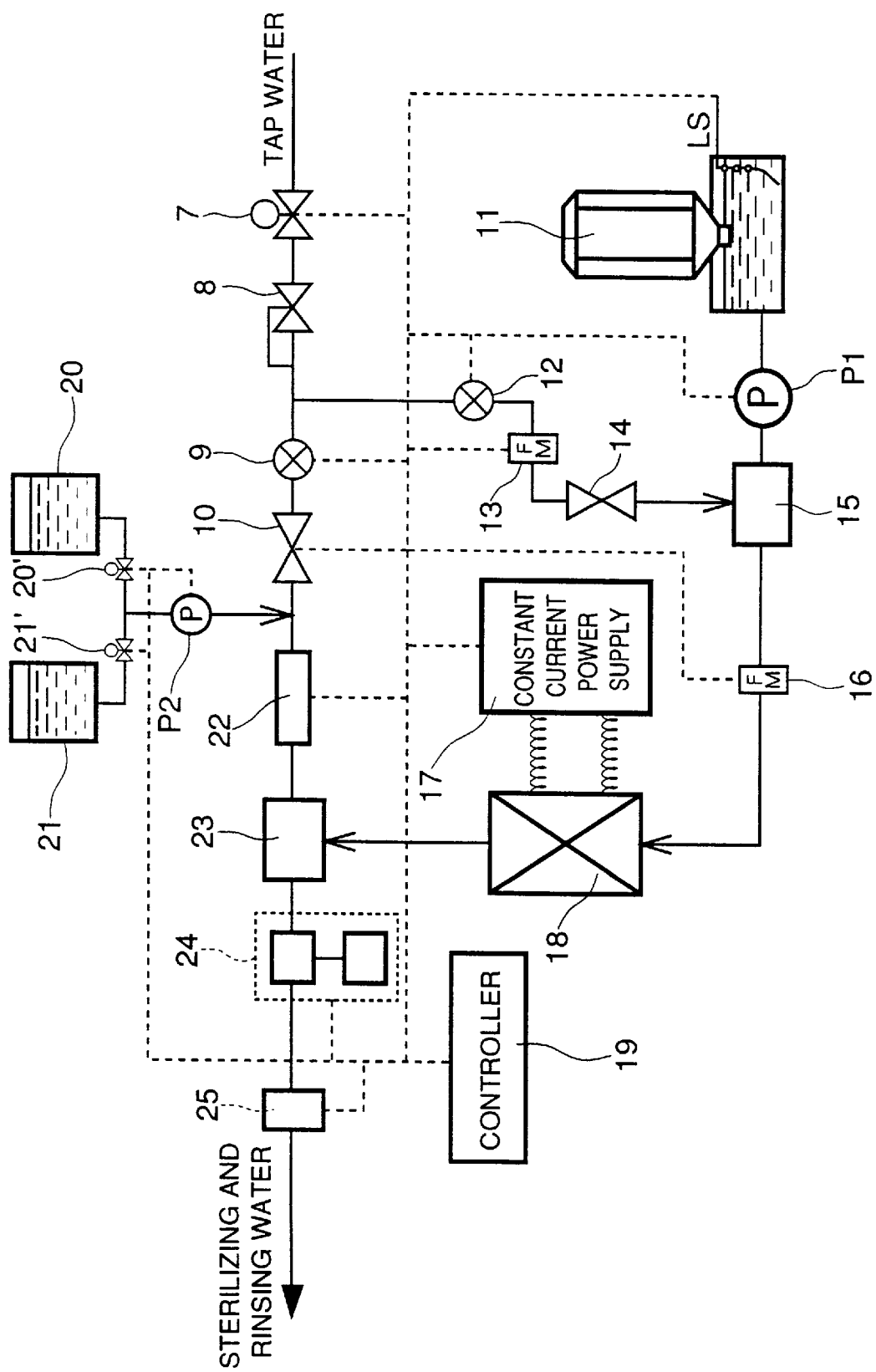
FIG. 3 is a system flow diagram showing the arrangement of the sterilizing and rinsing water generating apparatus of the embodiment according to the present invention.
Figure 4:
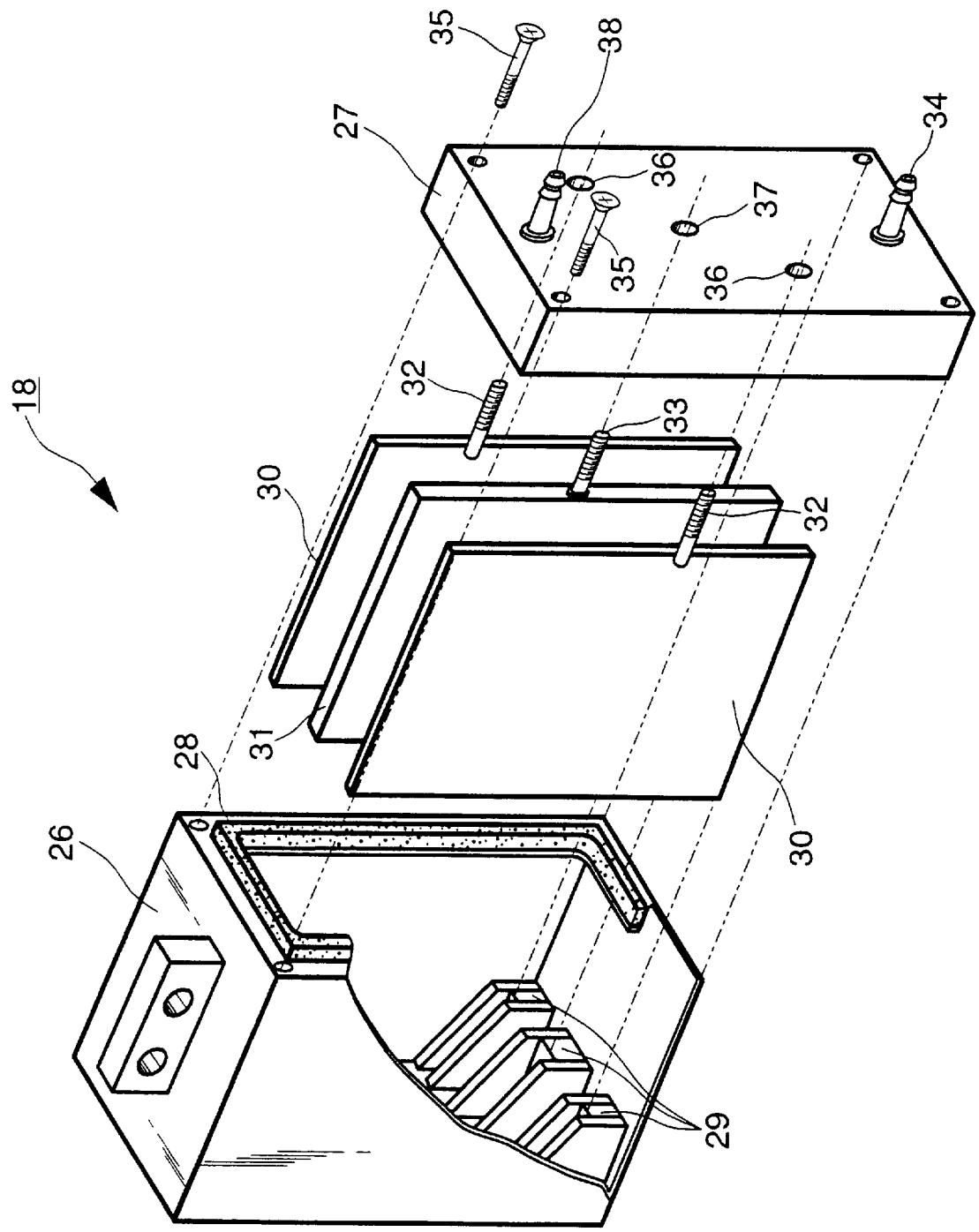
FIG. 4 is an exploded perspective views partly in cross section, showing an electrolyzer used in the sterilizing and rinsing water generating apparatus of the embodiment according to the present invention.
Figure 5:
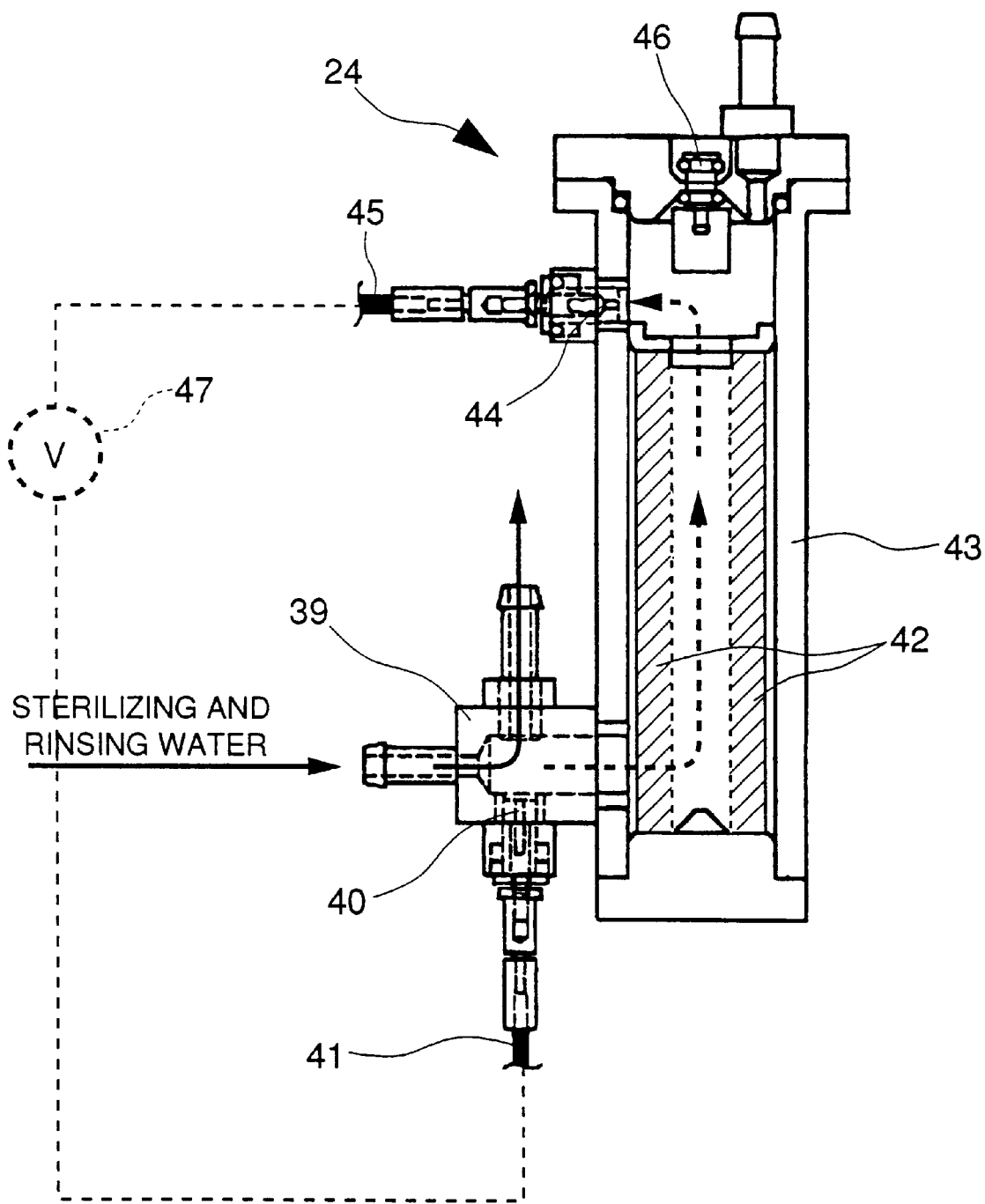
FIG. 5 is a side sectional view showing a device for measuring the concentration of free residual halogen used in the sterilizing and rinsing water generating apparatus of the embodiment according to the present invention.
Figure 6:
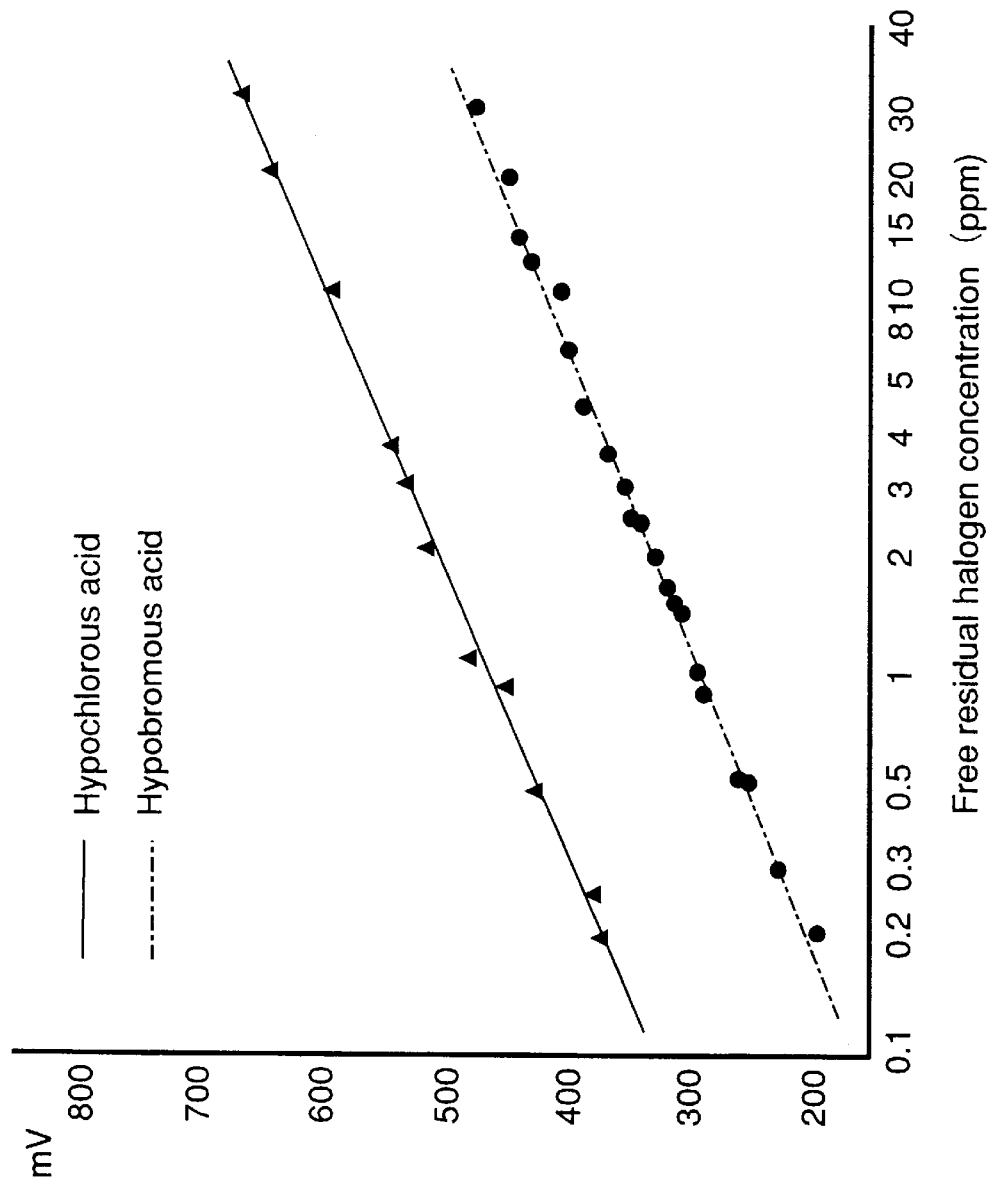
FIG. 6 is a graph showing the relationship between a hypohalogenous acid concentration and a voltage in a free residual halogen concentration measuring device used in the sterilizing and rinsing water generating apparatus of the embodiment according to the present invention.
Figure 7:
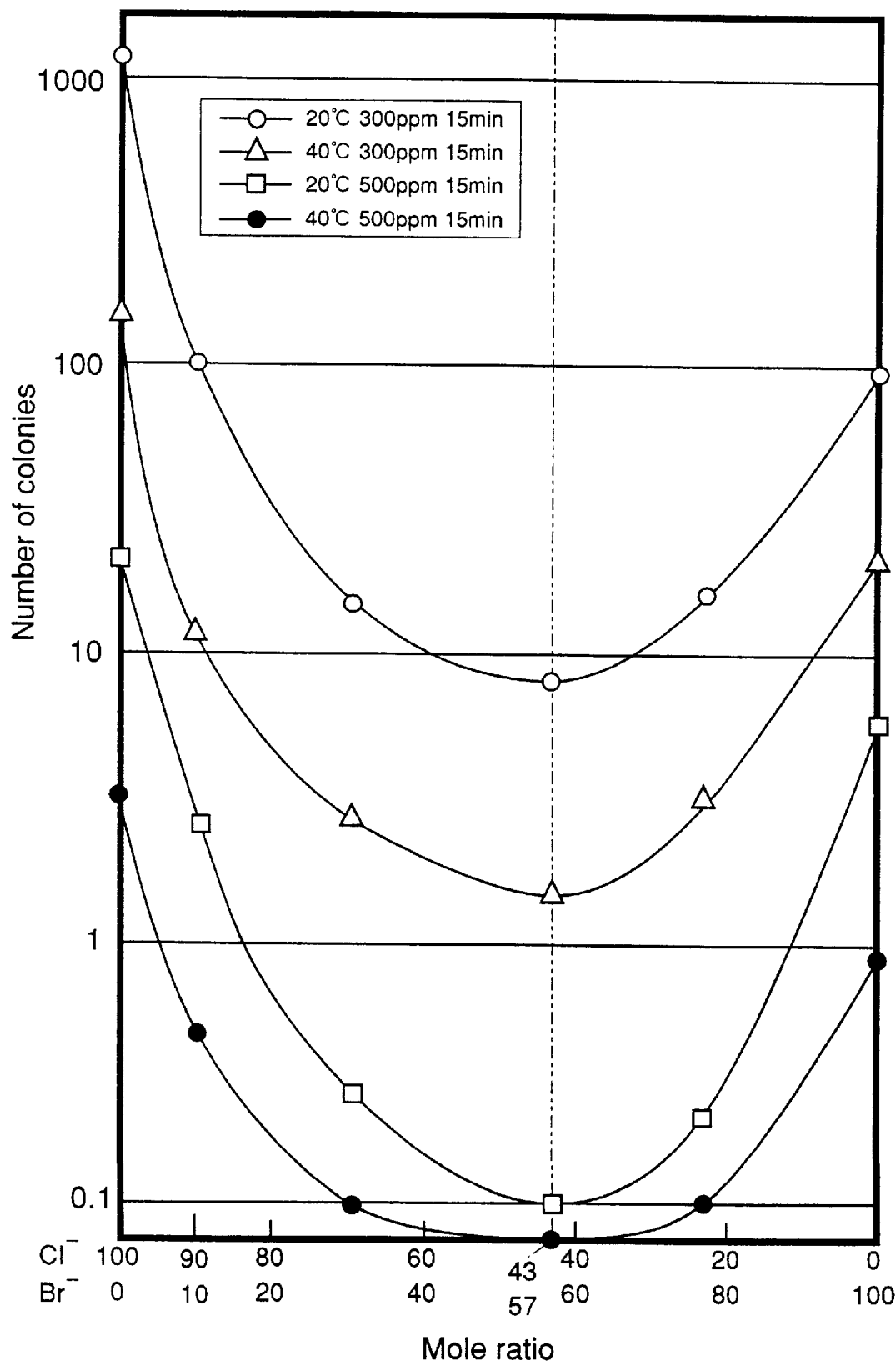
FIG. 7 is a graph showing the relationship among a sterilizing power for in *Bacillus subtilis* of the sterilizing and rinsing water generated by the sterilizing and rinsing water generating apparatus of the embodiment according to the present invention, a mixing ratio of bromide ions and chloride ions and a temperature.
Figure 8:
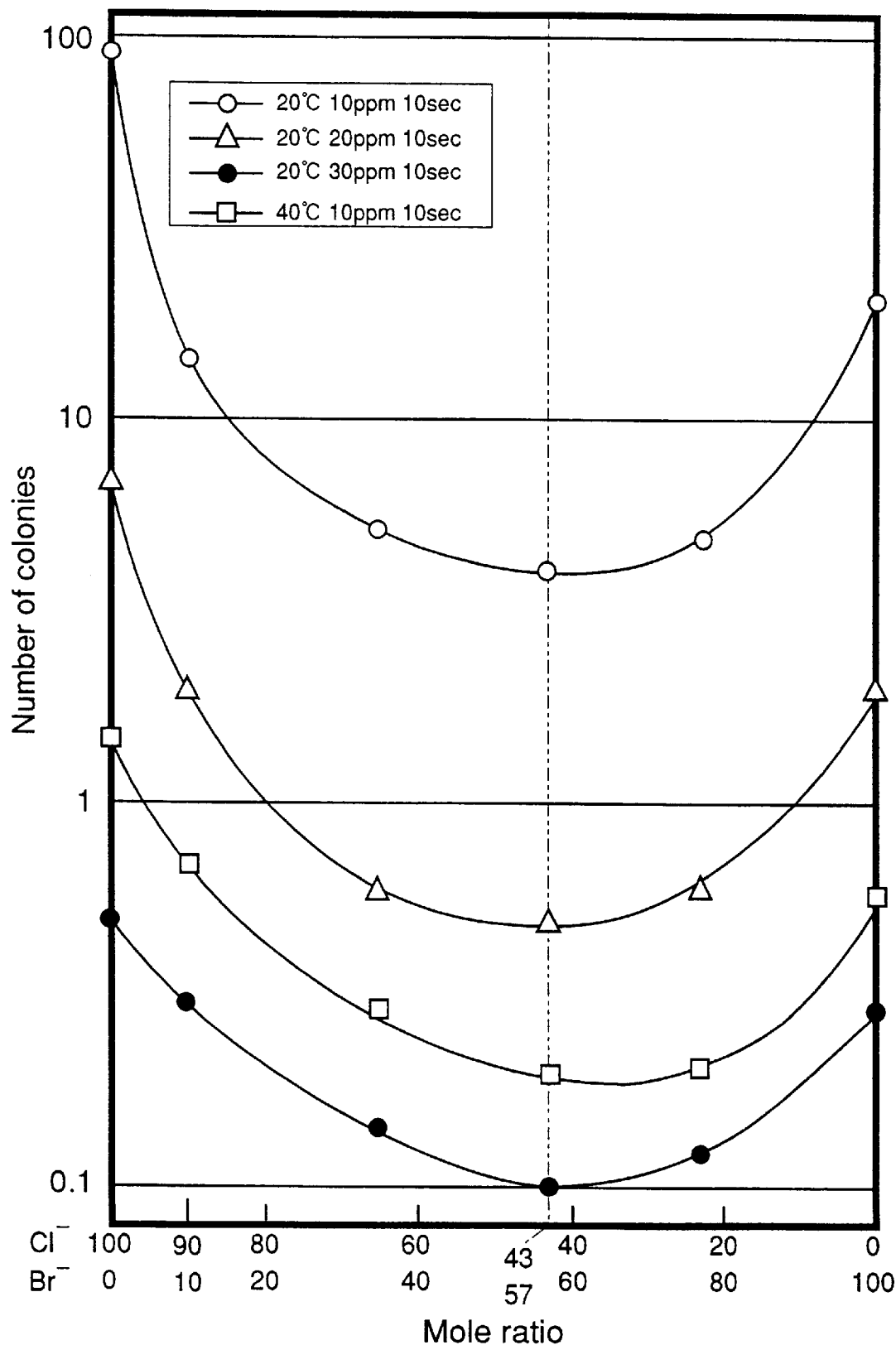
FIG. 8 is a graph showing the relationship among a sterilizing power for ordinary viable germs of the sterilizing and rinsing water generated by the sterilizing and rinsing water generating apparatus of the embodiment according to the present invention, a mixing ratio of bromide ions and chloride ions and a temperature.
Figure 9:
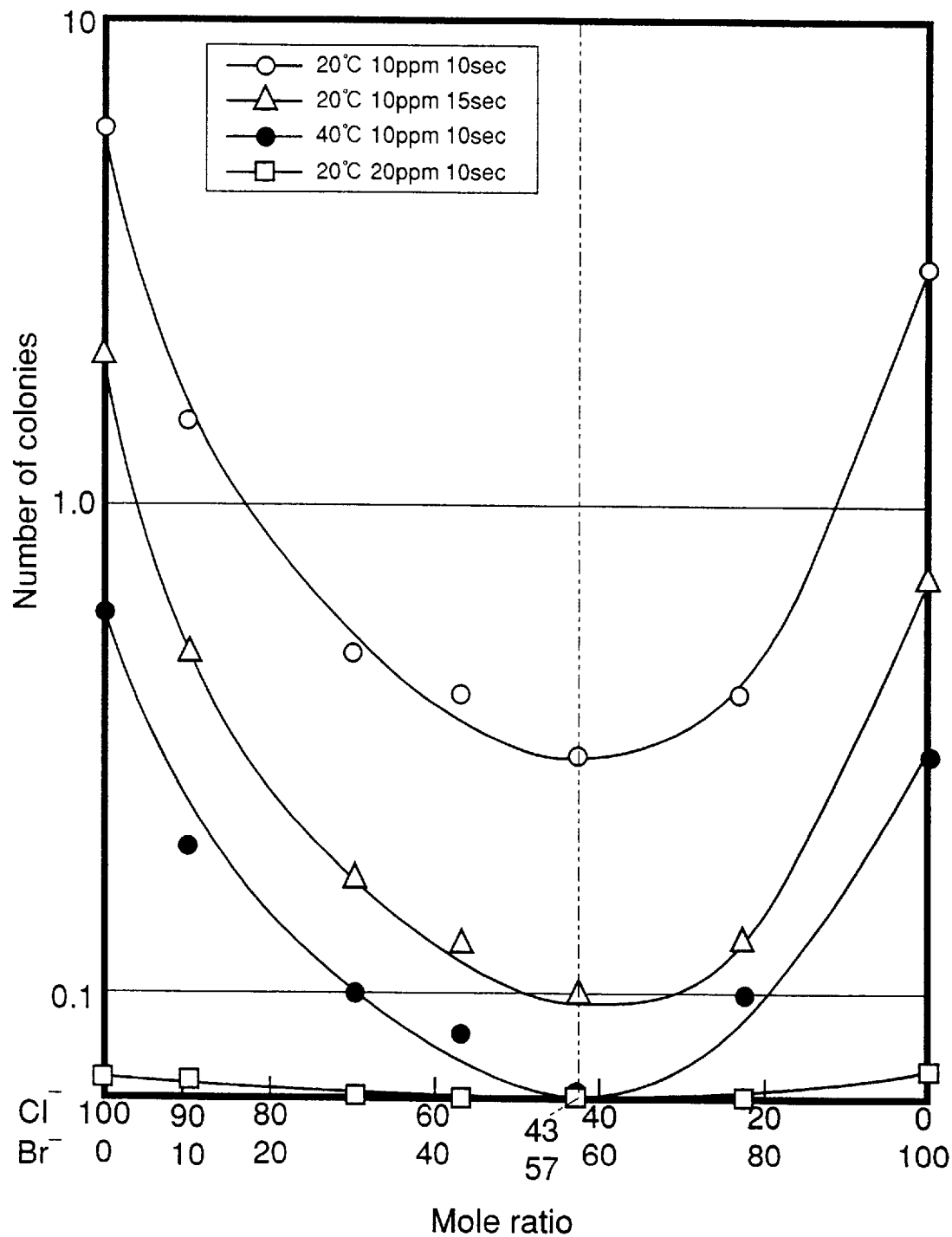
FIG. 9 is a graph showing the relationship among a sterilizing power for colon bacilli of the sterilizing and rinsing water generated by the sterilizing and rinsing water generating apparatus of the embodiment according to the present invention, a mixing ratio of bromide ions and chloride ions and a temperature.
Figure 10:
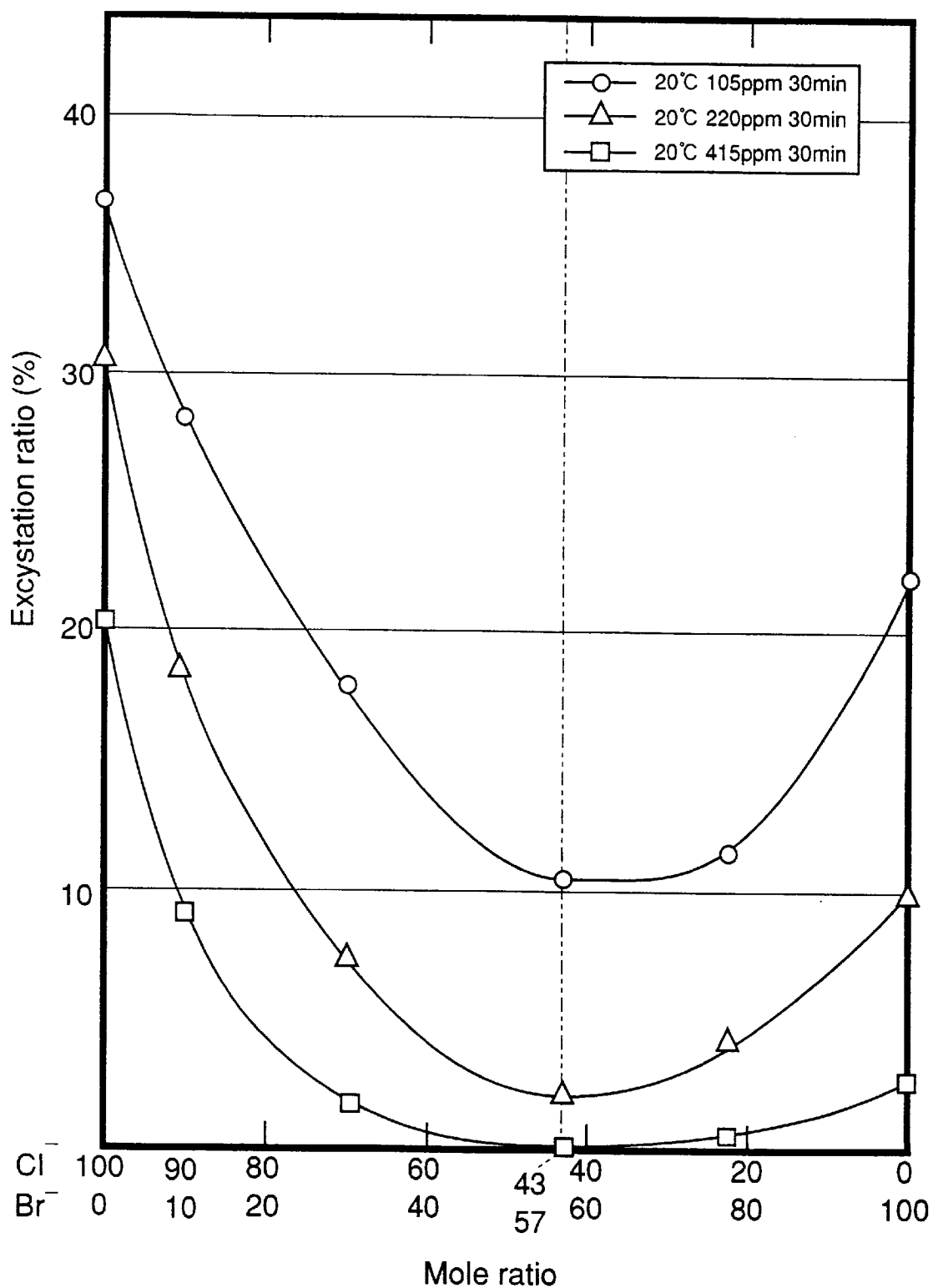
FIG. 10 is a graph showing the relationship between an excystation ratio of Cryptosporidium achieved by the sterilizing and rinsing water generated by the sterilizing and rinsing water generating apparatus of the embodiment according to the present invention and a mixing ratio of bromide ions and chloride ions.

FIG. 1 is a perspective view showing the outside appearance of a sterilizing and rinsing water generating apparatus of an embodiment according to the present invention; FIG. 2 is a side elevational view, partly in cross section, showing the inside arrangement of the sterilizing and rinsing water generating apparatus of the embodiment according to the present invention; FIG. 3 is a system flow diagram showing the arrangement of the sterilizing and rinsing water generating apparatus of the embodiment according to the present invention; FIG. 4 is an exploded perspective view partly in cross section, showing an electrolyzer used in the sterilizing and rinsing water generating apparatus of the embodiment according to the present invention; FIG. 5 is a side sectional view showing a device for measuring the concentration of free residual halogen used in the sterilizing and rinsing water generating apparatus of the embodiment according to the present invention; and FIG. 6 is a graph showing the relationship between the concentration of hypohalogenous acid and a voltage in the device for measuring the concentration of free residual halogen used in the sterilizing and rinsing water generating apparatus of the embodiment according to the present invention.

The sterilizing and rinsing water generating apparatus of the present invention has the outside appearance shown in FIG. 1. In the apparatus, a discharge port 2 for supplying sterilizing and rinsing water is disposed to a lower portion of the front surface of a generating apparatus main body 1 (hereinafter, referred to as a main body 1). A flexible pipe 3 is connected to the discharge port 2 and a shower port 5 is connected to the flexible pipe 3. A sensor (not shown) for sensing a human body such as a hand is provided with the shower port 5 so that the approach of the human body to the shower port 5 permits the sterilizing and rinsing water to automatically shower from the shower port 5.

A control panel 4 is disposed on the front surface of the main body 1 to display a state of the apparatus.

Numeral 6 in FIG. 1 denotes an openable/closable accommodating door for accommodating an electrolyte aqueous solution tank 11 in the apparatus, the tank 11 containing an electrolyte aqueous solution set to a prescribed concentration.

The interior of the main body 1 for generating the sterilizing and rinsing water of the embodiment is arranged as shown in FIGS. 2 and 3. Tap water, which will be used for dilution, is introduced into the apparatus from a lower portion of a side thereof through an electromagnetic valve 7 and a pressure reducing valve 8.

Accommodated in the interior of accommodating door 6 mounted on the main body 1 is the electrolyte aqueous solution tank 11 containing the aqueous solution which includes, in the embodiment, the electrolytes dissolved therein and set to the prescribed concentration to have a prescribed electric conductivity. The electrolyte aqueous solution is discharged from a lower portion of the electrolyte aqueous solution tank 11. A receiver pail is disposed to a lower portion of the electrolyte aqueous solution tank 11. A level sensor LS is located in the receiver pail in order to display the level of the electrolyte aqueous solution on the control panel 4 when the remaining amount thereof decreases.

As shown in FIGS. 2 and 3, an acid tank 21, which stores hydrochloric acid as inorganic acid set to a prescribed concentration, and an alkali tank 20, which stores a sodium hydroxide aqueous solution as an alkali aqueous solution set to a prescribed concentration, are disposed to a lower portion of the receiver pail. An electromagnetic valve 21' is disposed to the acid tank 21 and an electromagnetic valve 20' is disposed to the alkali tank 20, respectively. Acid or alkali is individually added to the tap water, which will be used to secondary dilution to be described below, from the acid tank 21 or the alkali tank 20 through a pump P2 so that the hydrogen ion concentration (pH) thereof is adjusted based on a signal from a controller 19 to be described later.

The electrolyte aqueous solution discharged into the receiver pail from the electrolyte aqueous solution tank 11 is supplied to a primary diluting unit 15 by a pump P1. A portion of the tap water is supplied to the primary diluting unit 15 from a branch flow passage disposed downstream of the pressure reducing valve 8 through a flow switch 12, a flow meter 13 and a constant flow rate orifice 14. The above process causes the electrolyte aqueous solution to be suitably diluted with the tap water and supplied to an electrolyzer 18 through a flow meter 16.

In the embodiment, a water flow passage provided with the flow meter 16 is disposed at a position higher than the discharge port of the electrolyzer 18 to thereby prevent the reverse flow of the water which has been electrolyzed and in which hypohalogenous acid has been produced.

As shown in FIG. 3, a flow switch 9, a constant flow rate orifice 10 and a temperature increasing heater 22 are disposed downstream of the pressure reducing valve 8. The temperature increasing heater 22 contains a thermometer for measuring the temperature of the tap water so that the tap water is increased to a prescribed temperature and then supplied to a secondary diluting unit 23 and dilutes the electrolyte aqueous solution which has been electrolyzed in the electrolyzer 18.

The tap water is arranged as a sterilizing and rinsing water which contains the hypohalogenous acid set to a prescribed concentration by being diluted at the secondary diluting unit 23. Then, the concentration of the hypohalogenous acid in the sterilizing and rinsing water and the hydrogen ion concentration therein are measured by a free residual halogen concentration sensor 24 and a pH sensor 25 and the sterilizing and rinsing water is discharged from the discharge port 2.

As shown by broken lines in FIG. 3, the respective units of the embodiment are connected to the controller 19 and controlled by it. The controller 19 controls the respective units based on a program in which the contents of control are previously described.

The electrolyzer 18 used in the embodiment is arranged as shown in FIG. 4. More specifically, a vinyl chloride cabinet 26 contains two cathode plates 30 which face each other across an anode plate 31 at prescribed spacings and the tap water is electrolyzed while flowing between the anode plate 31 and the cathode plates 30.

In the embodiment, nickel simple ferrite is used as the anode plate 31 because it is excellent in specific resistance, corrosion resistance, shock resistant strength and the like. The nickel simple ferrite is obtained by mixing nickel oxide as a divalent metal compound and ferric oxide at a prescribed ratio and baking the mixture under a suitable atmospheric condition. However, the present invention is not be limited thereto and other types of ferrite electrode or a titanium electrode covered with platinum may be used.

Although a titanium plate is used as the cathode plate 30 in the embodiment, the present invention is not be limited thereto and a ferrite electrode or a titanium electrode covered with platinum may be used likewise the anode plate 31.

The respective electrode plates 30 and 31 are inserted into inserting portions 29 disposed in the cabinet 26 so that they are disposed at the prescribed spacings. When the spacings between the electrode plates are too large, a voltage imposed between the electrode plates is increased and a power supply to be used is made expensive, whereas when they are too small, the throughput of the water processed by the electrolyzer 18 is reduced. Thus, the spacings are preferably set within a range of 1–10 mm and in particular 6 mm in the embodiment.

The opening of the cabinet 26 at an edge thereof is covered with vinyl chloride lid 27 which is fixed thereto by conical screws 35 through a packing 28. The cathode plates 30 are provided with electrode terminals 32 which are exposed to the outside through the holes 36 formed to the lid 27 and the anode plate 31 is provided with an electrode terminal 33 which is exposed to the outside through the hole 37 formed to the lid 27. Each of the electrode terminals 32, 33 is fixed to the lid 27 with an O-ring, circular washer and stainless steel nut. A constant current power supply 17 is connected to the electrode terminals 32, 33 as shown in FIG. 2 to thereby supply a prescribed current thereto. Electrolysis is carried out to the electrolyte aqueous solution supplied from the lower side of the respective electrode plates 30, 31 through an inlet joint 34 which is disposed at a lower position of the lid 27 and communicates with the interior of the cabinet 26. Then, the electrolyzed aqueous solution is discharged from an outlet joint 38 disposed at an upper position of the lid 27.

The free residual halogen concentration sensor 24 used in the embodiment is arranged as shown in FIG. 5. More specifically, the sensor 24 comprises a cylindrical case 43 containing a catalyst 42 for decomposing hypohalogenous acid in it, a measuring electrode 40 disposed to a cross port 39 so as to be exposed in the sterilizing and rinsing water and a reference electrode 44 disposed so as to be exposed in the cylindrical case 43. The measuring electrode 40 and the reference electrode 44 are connected to a microvolt meter 47 through cables 41, 45. Numeral 46 in the drawing denotes an air vent valve.

How and why the free residual halogen concentration sensor 24 senses the concentration of free residual halogen will be simply described. First, the space in the cylindrical case 43 is filled with sterilizing and rinsing water containing hypohalogenous acid.

The hypohalogenous acid in the sterilizing and rinsing water is approximately completely decomposed by the catalyst 42 and the interior of the cylindrical case 43 is filled with water in which almost no hypohalogenous acid exists.

The sterilizing and rinsing water containing hypohalogenous acid flows in the cross port 39 as shown by a solid arrow to thereby generate a minute voltage between the measuring electrode 40 exposed to the flow passage of the sterilizing and rinsing water and the reference electrode 44 exposed to the water, in which no hypohalogenous acid exists, in the cylindrical case 43. Since the relationship shown in FIG. 6 is established between the voltage and the concentration of the free residual hypohalogenous acid, the concentration of the free halogen remaining in the water can be sensed at any time by measuring the voltage with the microvolt meter 47. The voltage data measured by the microvolt meter 47 is outputted to the controller 19 so that it can sense the concentration of the free halogen remaining in the sterilizing and rinsing water at any time.

An operation of the sterilizing and rinsing water generating apparatus of the embodiment will be described below. When a hand as a human body approaches the shower port 5, the sensor (not shown) senses the human body and outputs a signal to the controller 19.

The flow switch 12 is opened in response to the signal so that a prescribed quantity of tap water flows into the primary diluting unit 15. At the same time, the electrolyte aqueous solution, which was discharged from the electrolyte aqueous solution tank 11 into the receiver pail, is supplied to the primary diluting unit 15 by the pump P1, suitably diluted with the tap water and supplied to the electrolyzer 18.

At the time, the flow rate of the primarily diluted electrolyte aqueous solution to be supplied to the electrolyzer 18 is measured by the flow meter 16.

In the embodiment, the weight ratio of sodium bromide and sodium chloride in the electrolyte aqueous solution stored in the electrolyte aqueous solution tank 11 is set to about 7:3 (the mole ratio of bromide ion and chloride ion is 57:43) so that the concentration of the electrolyte aqueous solution has the prescribed electric conductivity.

Although the electrolyte aqueous solution, in which sodium bromide and sodium chloride are premixed at the prescribed ratio and dissolved, is used in the embodiment, the present invention is not limited thereto. That is, the electrolyte aqueous solution tank 11 may be prepared for each of sodium bromide and sodium chloride a sodium bromide aqueous solution and a sodium chloride aqueous solution are individually supplied from the respective tanks thereof.

The electrolyte aqueous solution which was primarily diluted and is supplied to the electrolyzer 18 is electrolyzed between the electrode plates to thereby create the hypohalogenous acid of hypobromous acid and hypochlorous acid having a sterilizing capability and discharged to the secondary diluting unit 23.

When the flow switch 9 is opened by the controller 19, tap water, which was increased to a prescribed temperature (about 40° C. in the embodiment) and set to a prescribed flow rate while passing through the constant flow rate orifice 10 and the temperature increasing heater 22, is discharged to the secondary diluting unit 23. Then, the electrolyte aqueous solution, in which hypohalogenous acid was created and which was discharged from the electrolyzer 18, is mixed with the tap water and diluted to have the prescribed concentration of the hypohalogenous acid, discharged from the above discharge port 2 to the outside through the flexible pipe 3 and the shower port 5 so that it is used to sterilize and rinse a hand and the like.

At the time, the concentration of the hypohalogenous acid in the sterilizing and rinsing water discharged from the secondary diluting unit 23 is sensed by the free residual halogen concentration sensor 24 and the sensed data is outputted to the controller 19. With this operation, the ratio, at which the electrolyte aqueous solution having been electrolyzed is to be diluted by being mixed with the temperature increased tap water in the secondary diluting unit 23, is controlled by increasing or decreasing the quantity of the electrolyte aqueous solution to be mixed with the tap water so that the hypohalogenous acid has the prescribed concentration. When the prescribed concentration of the hypohalogenous acid cannot be obtained even if the quantity of the electrolyte aqueous solution is increased or decreased, the controller 19 increases or decreases the quantity of the tap water which will be used for dilution in the primary diluting unit 15 to thereby increase the electric conductivity of the electrolyte aqueous solution supplied to the electrolyzer 18 so that the concentration of the hypohalogenous acid created by the electrolyzer 18 is increased. Otherwise, the controller 19 decreases the discharge quantity of the pump P1 to thereby increase the period of time during which the electrolyte aqueous solution passes through the electrolyzer 18 so that the concentration of the created hypohalogenous acid is increased.

When the prescribed concentration of the hypohalogenous acid cannot be obtained even by the above controls, the discharge of the sterilizing and rinsing water is stopped and an abnormal state is displayed on the control panel 4.

In the embodiment, the hydrogen ion concentration in the sterilizing and rinsing water discharged from the discharge port 2 is sensed by the pH sensor 25 at any time. The controller 19 suitably controls the pump P2 so that it adds the aqueous solution of hydrochloric acid as inorganic acid or the aqueous solution of sodium hydroxide from the acid tank 21 or the alkali tank 20 to the tap water used to the secondary dilution so as to set the pH of the sterilizing and rinsing water sensed by the pH sensor 25 to 6–8 at all times.

In the embodiment, the sterilizing and rinsing water is discharged from the discharge port 2 in the quantity of about one liter in about 15 seconds and the discharge thereof is automatically stopped. When the sterilizing and rinsing water is discharged, the concentration of the hypohalogenous acid contained therein is set such that it is increased at the beginning of the discharge and then lowered for a prescribed period of time before the discharge is ended to permit the sterilizing and rinsing water to be used for rinsing. However, the present invention is not limited thereto.

Although the electrolyte aqueous solution is primarily diluted and then supplied to the electrolyzer 18 in the embodiment as described above, the present invention is not limited thereto and the electrolyte aqueous solution may be supplied to the electrolyzer 18 without being diluted by closing the flow switch 12.

Sterilizing and rinsing waters were generated by means of the sterilizing and rinsing water generating apparatus of the embodiment by variously changing the ratio of sodium bromide and sodium chloride to be used as well as using tap water for dilution which was not heated to the prescribed temperature and tap water for dilution which was heated to the prescribed temperature. A test was carried out to compare the sterilizing powers of the thus obtained sterilizing and rinsing waters and Table 1 shows a result of the test. Table 1

In the test of the sterilizing and rinsing waters, germ liquid specimens were prepared as follows: in the test of the sterilizing and rinsing waters to *Bacillus subtilis* which formed spores, *Bacillus subtilis* RIMD 0225015 was previously cultured and mixed with the sterilizing and rinsing waters which were diluted with Phosphate buffered saline (PBS) when the experiment was executed so that they are obtained in an amount of $10^6$ CFU/ml; and in the test of the sterilizing and rinsing waters to ordinary viable germs and colon bacilli, mixed waters in which they were contained in the amounts $6.1 \times 10^6$ and $7.2 \times 10^6$, respectively were used.

The sterilizing and rinsing water was made in such a manner that: the electrolyte aqueous solution tanks 11, which contained electrolyte aqueous solutions including sodium bromide and sodium chloride at various ratios and having a prescribed electric conductivity, were prepared; the electrolyte aqueous solution tanks 11 were loaded on the sterilizing and rinsing water generating apparatus; the electrolyte aqueous solution in each of the electrolyte aqueous solution tanks 11 was electrolyzed under the same electrolyzing conditions, the resulting electrolyzed aqueous solution was diluted with germ-reduced water so that a free residual halogen concentration (when converted into chlorine) was adjusted to 300 ppm and 500 ppm as to *Bacillus subtilis* and to 10 ppm, 20 ppm and 30 ppm as to ordinary viable germs and colon bacilli.

The sterilizing and rinsing waters having the above respective free residual halogen concentrations which were obtained at the respective ratios of sodium bromide and sodium chloride were put into test tubes in a quantity of 9 ml and each 1 ml of the germ liquid specimens were added to the sterilizing and rinsing waters and stirred. Then, test liquids were taken out from the test tube in a quantity of 1 ml after 15 minutes as to *Bacillus subtilis*, after 10 seconds as to ordinary viable germs and after 10 seconds and partially after 15 seconds as to colon bacilli and diluted to 10 times, 100 times and 1000 times, respectively. The test liquids were cultured in standard agar culturing regions at 35° C. for 48 hours as to *Bacillus subtilis* and ordinary viable germs and in desoxycholate agar culturing regions 37° C. for 24 hours as to the group of colon bacilli, respectively. A test for counting the number of colonies at the respective test culturing regions was executed thee times, respectively and the average value of the colonies was determined.

After the sterilizing and rinsing waters which were adjusted to the above respective free residual halogen concentrations and put into the test tubes in the quantity of 9 ml, the test tubes were placed in thermostats set to about 20° C. and 40° C. and the germ liquid specimens were added to the sterilizing and rinsing waters when their temperatures reached 20° C. and 40° C.

When similar processing was executed using germ-reduced water in place of the sterilizing and rinsing waters as control, the quantity of the *Bacillus subtilis* was $3.0 \times 10^5$, the quantity ordinary viable germs was $4.8 \times 10^4$ and the quantity of colon bacilli was $4.5 \times 10^5$.

Further, there was prepared a test liquid specimen containing 320–350 pieces of Cryptosporidium which formed an oocyst wall and had very strong tolerance to medicines and the like, similarly to the spores of *Bacillius subtilis*. The electrolyte aqueous solution tanks 11, which contained electrolyte aqueous solutions including sodium bromide and sodium chloride at various ratios and having a prescribed electric conductivity, were prepared and loaded on the sterilizing and rinsing water generating apparatus likewise the above case. The electrolyte aqueous solution in each of the electrolyte aqueous solution tanks 11 was electrolyzed under the same electrolyzing conditions and the resulting electrolyzed aqueous solution was diluted with germ-reduced water so that a free residual halogen concentration (when converted into chlorine) was adjusted to 105 ppm, 220 ppm and 415 ppm. The germ liquid specimen was added to the sterilizing and rinsing waters having the respective ratios of bromine ions and chlorine ions and stirred for a prescribed period of time (30 minutes in the embodiment) and an excystation ratio was measured by counting the number of Cryptosporidium in an excystation state.

The term "excystation" means the state that the oocyst wall of Cryptosporidium opens and sporozoite acting as a source of infection is discharged therefrom. The excystation ratio is a value represented by a percentage which shows the Cryptosporidium in an excystation state counted under a microscope when the initial state of the Cryptosporidium is represented by 100% and an excystation ratio nearer to 0% indicates a better sterilized state.

FIG. 7, FIG. 8, FIG. 9 and FIG. 10 are graphs showing the major results of experiments executed to *Bacillus subtilis*, ordinary viable germs and colon bacilli shown in Table 1 and the above Cryptosporidium.

It can be found from FIG. 7, FIG. 8, FIG. 9 and FIG. 10 that a higher sterilizing capability can be obtained by using simple bromide ions resulting from sodium bromide rather than using simple chlorine ions resulting from sodium chloride in not only *Bacillus subtilis* which forms spores and Cryptosporidium but also in ordinary viable germs and colon bacilli. Further, it can be found that when these bromide ions and chlorine ions are mixed and the mole ratio of the resultant mixture is set to 57:43 or a value in the vicinity of it, there is obtained a sterilizing power which is higher than that of the simple bromide ions and highest among the mixing systems.

The sterilizing capability in the above mixed systems is greatly improved by the addition of a slight amount of bromide ion to chlorine ion. It is conceived that the improvement results from that ion exchange is executed by the hypochlorous acid created by the electrolysis and the chloride ion and accordingly hypobromous acid which has a high sterilizing power and is stable even in a weak alkali region is created, as shown by the following chemical formula.

$$HClO + Br^- \leftrightarrow HBrO + Cl^-$$

Figure 11:
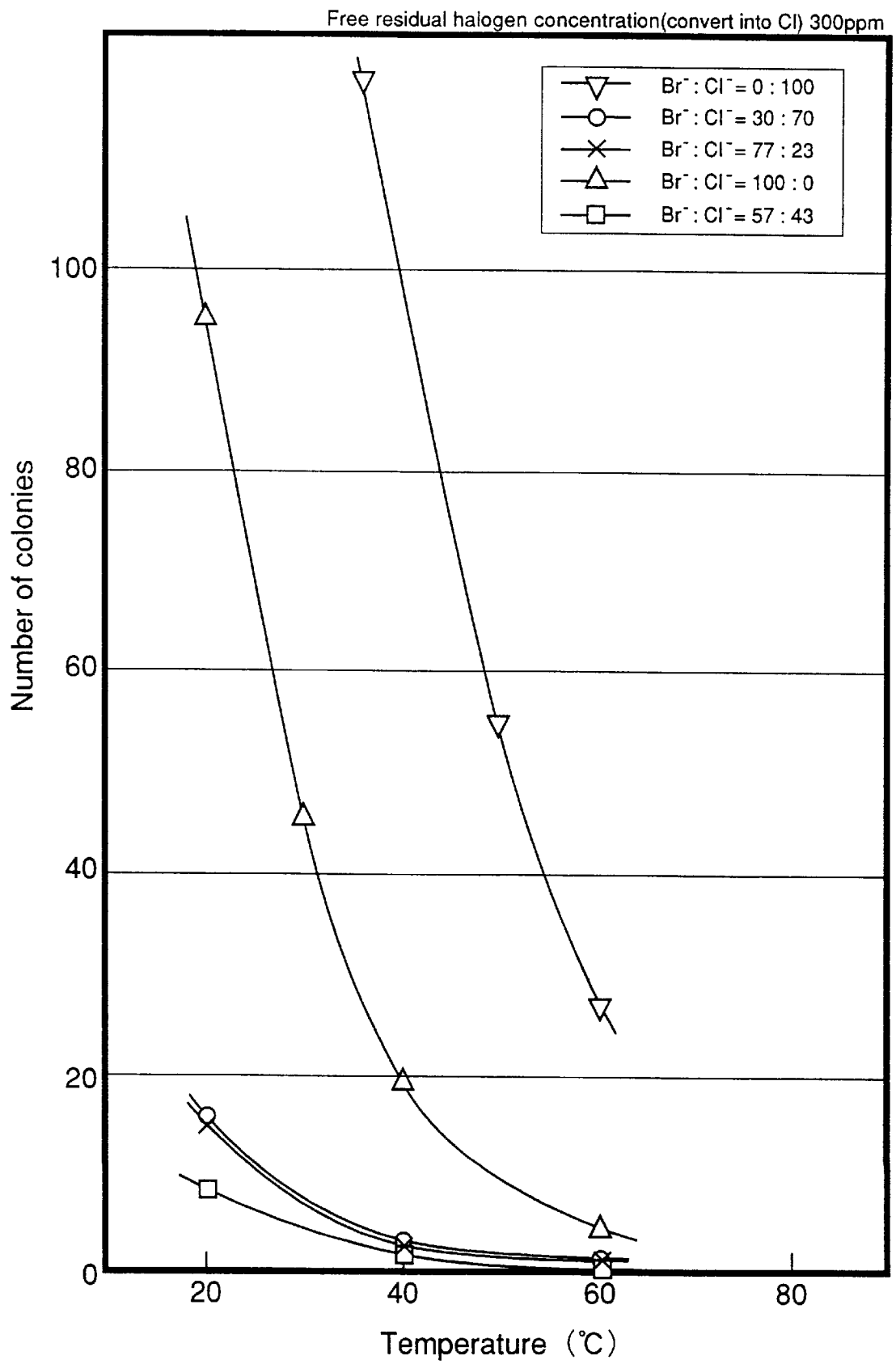
FIG. 11 a graph showing the relationship among a sterilizing power for *Bacillus subtilis* the sterilizing and rinsing water generated by the sterilizing and rinsing water generating apparatus of the embodiment according to the present invention, respective mixing ratios of bromide ions and chloride ions and a temperature.

FIG. 11 shows the result of test of the relationship between the sterilizing power of the sterilizing and rinsing water to *Bacillus subtilis* and the temperature thereof as the relationship between the temperature of the sterilizing and rinsing water and the sterilizing power thereof.

The test was carried out at 20° C. and 40° shown in the above test conditions as well as at 60° C. A free residual halogen concentration was set to 300 ppm when converted into chlorine and a processing was set to 15 minutes.

It can be found from the result shown in FIG. 11 that an increase in the temperature of the sterilizing and rinsing water increases the sterilizing power thereof at any ratio of bromine ions and chlorine ions and the sterilizing power is greatly increased at 20–40° C.

That is, when the above result is observed from an opposite point of view, it can be found that a stable sterilizing power can be obtained without causing a large reduction of the sterilizing power even if the temperature of the sterilizing and rinsing water is lowered by setting the mole ratio of bromine ions and chlorine ions to 57:43 or a value in the vicinity of it.

It is contemplated that the sterilizing power is improved in such a process that the decomposing reaction of the hypohalogeneous acid contained in the sterilizing and rinsing water is increased by the increased temperature of the sterilizing and rinsing water and accordingly free radicals are more created by the decomposing reaction. From the mentioned above, in the creation of hypohalogeneous acid by the above electrolyzing apparatus, if the water electrolyzed by the electrolyzing apparatus is preheated to a prescribed temperature when it is electrolyzed or when there is a time before it is supplied to the outside, the hypohalogeneous acid is sometimes decomposed before it is supplied to the outside and an excellent sterilizing power cannot be obtained. Thus, when the water is supplied to the outside for use, it is preferable to instantaneously increase the temperature thereof by diluting it with tap water which is preheated to a prescribed temperature.

Although these sterilizing and rinsing waters are heated to 40° C. in the embodiment, the present invention is not limited thereto and their temperature may be suitably selected in accordance with an object to be sterilized and rinsed. More specifically, when the object to be sterilized and rinsed is a human body, food and the like, it is preferable to set the temperature to 30° C. to 50° C. because there is a possibility that the human body gets burned or the food is deteriorated. Whereas, when the object to be sterilized and rinsed is equipment, it is preferable to set the temperature to a range of 30° C. to 70° C.

Figure 12:
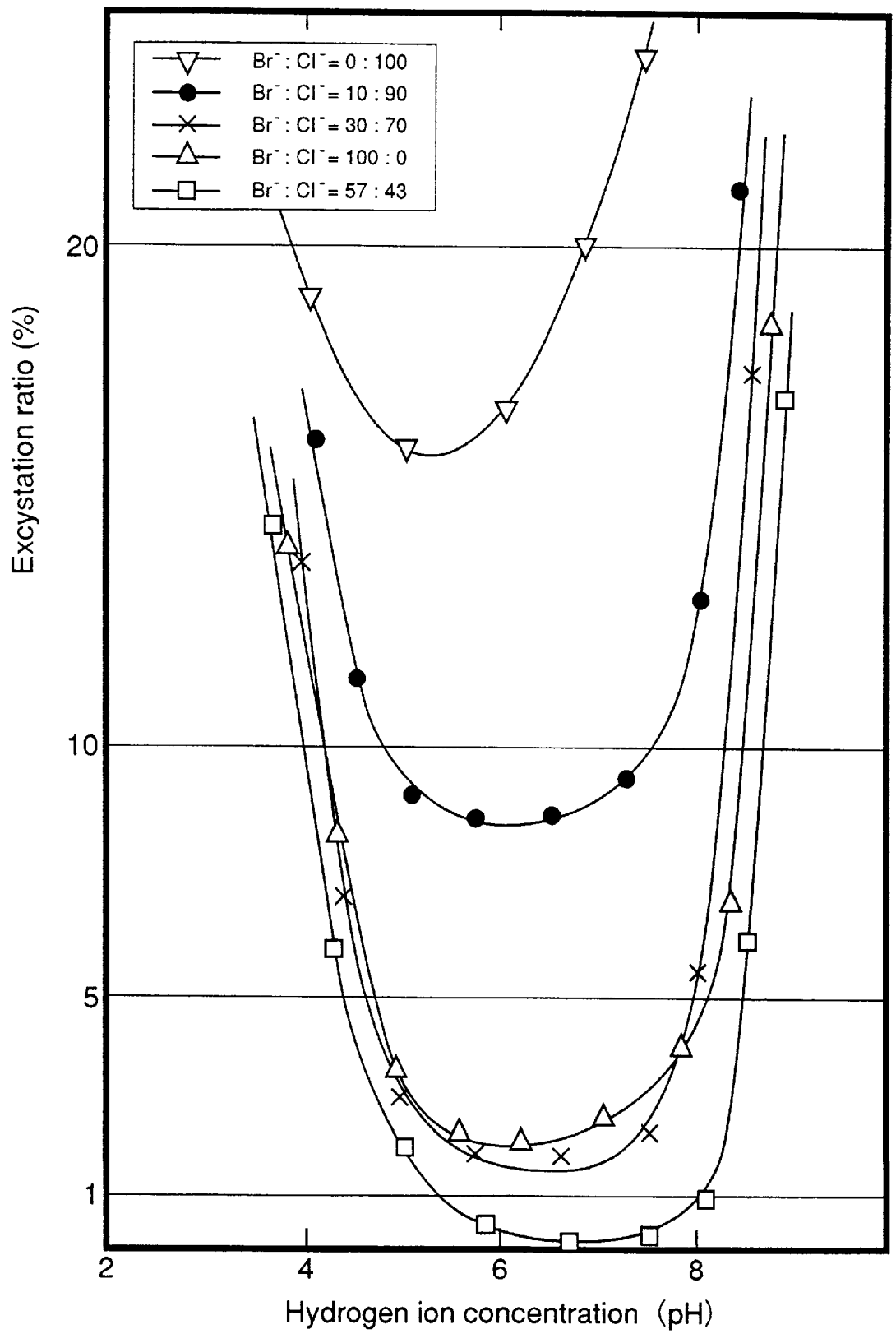
FIG. 12 is a graph showing the relationship between an excystation ratio of Cryptosporidium achieved by the sterilizing and rinsing water generated by the sterilizing and rinsing water generating apparatus of the embodiment according to the present invention, a hydrogen ion concentration and respective mixing ratios of bromide ions and chloride ions.

FIG. 12 shows the result of test executed using Cryptosporidium as an example as to the relationship between the sterilizing power and a hydrogen ion concentration.

The test was carried out using sterilizing and rinsing waters, which had a free residual halogen concentration set to about 200 ppm when converted into chlorine and a liquid temperature set to 20° C. and contained bromine ions and chlorine ions set to respective ratios, and adjusting the hydrogen ion concentration of the sterilizing and rinsing water to respective hydrogen ion concentrations by means of hydochloric acid as inorganic acid or sodium hydroxide.

From the result shown in FIG. 12, it can be found that: a higher sterilizing power can be obtained in a wider region of the hydrogen ion concentration as compared with conventional simple bromine ions by setting the mole ratio of bromine ions and chlorine ions to 57:43 or a value in the vicinity if it; and, in addition to the above, a sterilizing power larger than the maximum sterilizing power of the conventional simple bromine ions can be obtained in a range of the hydrogen ion concentration of 5–8. In particular, it can be found that a high sterilizing power is substantially stably obtained in the hydrogen ion concentration of 6–8 which is a neutral region where skin roughness and the damage of a rinsing vessel, piping and the like which are in contact with the sterilizing and rinsing water can be reduced.

With the arrangement of the embodiment described above, the sterilizing and rinsing water discharged from the shower port 5 is arranged as the sterilizing and rinsing water by the electrolysis in which the ratio of bromine ions and chlorine ions which are supplied by an additive halide is adjusted to approximately 57:43. Accordingly, there can be obtained the sterilizing and rinsing water which has not only a higher sterilizing power as compared with that of the conventional simple bromine ions but also the highest sterilizing power among these mixed systems. Further, the sterilizing power of the sterilizing and rinsing water can be more increased when it is supplied to the outside after the temperature thereof increased as well as since the hydrogen ion concentration of the sterilizing and rinsing water is always maintained to 6–8, the high sterilizing power can be stably obtained.

While the present invention has been described above with reference to the accompanying drawings, the present invention is by no means limited to the above embodiment and it goes without saying that various changes and additions can be made without departing from the gist of the present invention.

Although the sterilizing and rinsing water is prepared by diluting the electrolyte aqueous solution containing hypohalogeneous acid which is created by the electrolysis, the present invention is not limited thereto and the electrolyte aqueous solution having been electrolyzed may be directly used as the sterilizing and rinsing water.

Although sodium chloride and sodium bromide are used as a halide in the embodiment, the present invention is not limited thereto and a halide of other alkali metal such as, for example, potassium, lithium, etc. and a halide of magnesium, calcium, etc. as alkaline earth metal may be used and they may be suitably selected depending upon the cost of the halide and the like.

Although the temperature of the sterilizing and rinsing water is increased by heating the tap water used to secondary dilution in the embodiment, the present invention is not limited thereto and the temperature may be increased by other method, for example, by heating the sterilizing and rinsing water which was diluted and set to a prescribed concentration.

The present invention achieve the following advantages.

(a) It has been demonstrated that when the mole ratio of bromide ions and chloride ions in the water is set to 57:43 or a value in the vicinity of it, the sterilizing capability of the resultant sterilizing and rinsing water can be made higher than that of the sterilizing and rinsing water using simple bromide ions and further there can be obtained the highest effect among the systems containing the mixture of bromide ions and chloride ions.

Accordingly, it has been made possible to effectively sterilize not only various types of germs but also germs forming spores in a short time by using the mixing ratio.

(b) The sterilizing and rinsing water which is obtained by setting the mole ratio of bromide ions and chloride ions in the water to 57:43 or a value in the vicinity of it has the highest sterilizing capability in the region of pH 6–8.

More specifically, the above mole ratio is the most effective ratio in the overall region of pH 6–8 which is a neutral region in which hands are difficult to become rough as well as a rinsing vessel, discharge pipe and various types of equipment which are in contact with the sterilizing and rinsing water are difficult to be corroded.

(c) When the temperature of the sterilizing and rinsing water to be supplied to the outside is increased and caused to come into contact with an object to be sterilized, it is possible to maintain the sterilizing power of the sterilizing and rinsing water for a prescribed period of time and then to increase the sterilizing capability thereof instantaneously and cause it to act to the object to be sterilized.

(d) Since a larger quantity of sterilizing and rinsing water can be generated by electrolyzing a smaller quantity of water, the apparatus can be reduced in size as well as the sterilizing and rinsing water having the stable hypohalogeneous acid can be supplied and sterilization can be carried out sufficiently.

(e) Bromide salt and chloride salt are mixed with water at a prescribed ratio, bromide ions and chloride ions coexist in the water at the mole ratio of 57:43 or a value in the vicinity of it. Accordingly, when hypochlorous acid and hypobromous acid are created by electrolyzing the water and the free residual halogen concentration of the water is set to a prescribed value, the sterilizing capability of the resultant sterilizing and rinsing water can be made higher than that of the sterilizing and rinsing water using simple bromide ions and achieve the highest sterilizing capability among the systems containing the mixture of bromide ions and chloride ions. In addition, the sterilizing and rinsing water can effectively sterilize germs which form spores in a short time.

(f) The thus generated sterilizing and rinsing water has a hydrogen ion concentration (pH) maintained to pH 6–8 at all times that have the highest sterilizing capability and a higher sterilizing force than that of the sterilizing and rinsing water using simple bromine ions. Accordingly, the best sterilizing force can be drawn out of the resultant sterilizing and rinsing water and an effective sterilization can be carried out.

(g) Since the sterilizing and rinsing water supplied from the sterilizing and rinsing water apparatus is heated to the prescribed temperature and then caused to come into contact with an object to be sterilized, the sterilizing power thereof can be more increased.

What is claimed is:

1. A method for controlling the generation and delivery of sterilizing and rinsing water comprising increasing the electric conductivity of water by adding to the water halide electrolytes in a mole ratio of bromide ions to chloride ions of about 57:43, creating hypohalogenous acid by electrolyzing the water between an anode plate and a cathode, measuring the hydrogen ion concentration of the electrolyzed water and adjusting the dilution thereof by addition of aqueous acid or alkali so that the pH is within a range of 6–8, delivering said generated sterilizing and rinsing water to an end use, and stopping the delivery of said sterilizing and rinsing water should the pH fall outside the range of 6–8.

2. A method according to claim 1, and including the step of heating the sterilizing and rinsing water prior the delivery thereof.

3. A method according to claim 1, and including the step of adding a dilute aqueous solution of an inorganic acid or alkali to the water in order to adjust the hydrogen ion concentration thereof.

4. Apparatus for generating and delivering sterilizing and rinsing water, comprising:

water supply for supplying water;

mixer disposed at a prescribed position in said water supply for mixing bromide salt and chloride salt to the water or discharged water at a prescribed ratio so that the mole ratio of the bromine ions and the chloride ions in the water is set to about 57:43;

electrolyzing cell disposed downstream of said electrolyte mixer and having an anode plate and a cathode plate;

a water supply for diluting the electrolyzed water;

free residual halogen concentration sensor for measuring the free residual halogen concentration in the diluted water;

controller for controlling the dilution of the water based on the free residual halogen concentration sensed by said free residual halogen concentration sensor so that the free residual halogen concentration in the water is set to a prescribed value;

a sensor for measuring the hydrogen ion concentration of the diluted water;

adder for adding inorganic acid or an alkali aqueous solution to the water, wherein said controller maintains the pH of the water at 6–8 by adding inorganic acid or alkali aqueous solution to the water via said adder means based on the hydrogen ion concentration measured by said hydrogen ion concentration sensor;

means for delivering the water to an end use; and a valve controlled by said hydrogen ion concentration sensor for stopping the delivery of said sterilizing and rinsing water should pH thereof fall outside the range of 6–8.

5. Apparatus according to claim 4, and further comprising a heater for heating the dilution water to a prescribed temperature.

* * * * *

UNITED STATES PATENT AND TRADEMARK OFFICE
CERTIFICATE OF CORRECTION

PATENT NO. : 6,113,853                                                                                  Page 1 of 1
DATED : September 5, 2000
INVENTOR(S) : Shinichi Nakamura et al.

It is certified that error appears in the above-identified patent and that said Letters Patent is hereby corrected as shown below:

<u>Column 14,</u>
Line 48, insert -- the -- after "should"

Signed and Sealed this

Seventh Day of May, 2002

Attest:

*Attesting Officer*

JAMES E. ROGAN
*Director of the United States Patent and Trademark Office*